US00PP33221P2

(12) United States Plant Patent
van Langen

(10) Patent No.: US PP33,221 P2
(45) Date of Patent: Jun. 29, 2021

(54) ***ECHEVERIA* PLANT NAMED 'TSAECH1824'**

(50) Latin Name: ***Echeveria* hybrid**
Varietal Denomination: TSAECH1824

(71) Applicant: Tosjami B.V., Heerhugowaard (NL)

(72) Inventor: Gerard van Langen, Heerhugowaard (NL)

(73) Assignee: Tosjami B. V., Heerhugowaard (NL)

( * ) Notice: Subject to any disclaimer, the term of this patent is extended or adjusted under 35 U.S.C. 154(b) by 0 days.

(21) Appl. No.: 16/873,496

(22) Filed: Apr. 21, 2020

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 5/12; A01H 5/00
See application file for complete search history.

(56) References Cited

PUBLICATIONS

PLUTO UPOVROM Plant Variety Database Sep. 11, 2020 Citation for 'TSAECH1824' as per QZ PBR 20183002; Feb. 16, 2019; 1 page.*

* cited by examiner

*Primary Examiner* — Kent L Bell
(74) *Attorney, Agent, or Firm* — Samuel R. McCoy, Jr.

(57) ABSTRACT

A new and distinct *Echeveria* plant named 'TSAECH1824' which is characterized by an abundance of small succulent foliage tightly held in a compact stemless rosette, moderately glaucous foliage, foliage that is colored between blue-grey and greyed-green and lightly suffused with a lilac coloration and conspicuously margined and tipped pink, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1824'.

BACKGROUND OF THE INVENTION

Parentage: 'TSAECH1824' is a seedling selection resulting from the controlled pollination of an unnamed *Echeveria lilacina* plant (not patented), the seed parent, with *Echeveria* hybrid 'Perle von Nurnberg' (not patented), the pollen parent. The crossing was made by the inventor in the spring of 2015 at a commercial greenhouse in Heerhugowaard, the Netherlands. In the spring of 2016, one seedling resulting from the cross of 2015 was observed to exhibit unique growth and foliage characteristics and was isolated for further evaluation in order to confirm the distinctness and stability of the characteristics first observed. Upon confirmation of distinctness and stability, 'TSAECH1824' was selected for commercialization.

Asexual Reproduction: Asexual reproduction of the new cultivar 'TSAECH1824', by way of rooting leaf cuttings, was first initiated in the autumn of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1824' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1824'. These characteristics in combination distinguish 'TSAECH1824' as a new and distinct *Echeveria* cultivar:

1. 'TSAECH1824' exhibits an abundance of relatively small succulent foliage which is tightly held in a compact, stemless rosette; and
2. 'TSAECH1824' exhibits moderately glaucous foliage, the color of which has a general appearance of a mixture between blue-grey and greyed-green and lightly suffused with a lilac coloration; and
3. 'TSAECH1824' exhibits foliage that is conspicuously margined and tipped pink.

BOTANICAL DESCRIPTION OF THE PLANT

Figure 1:
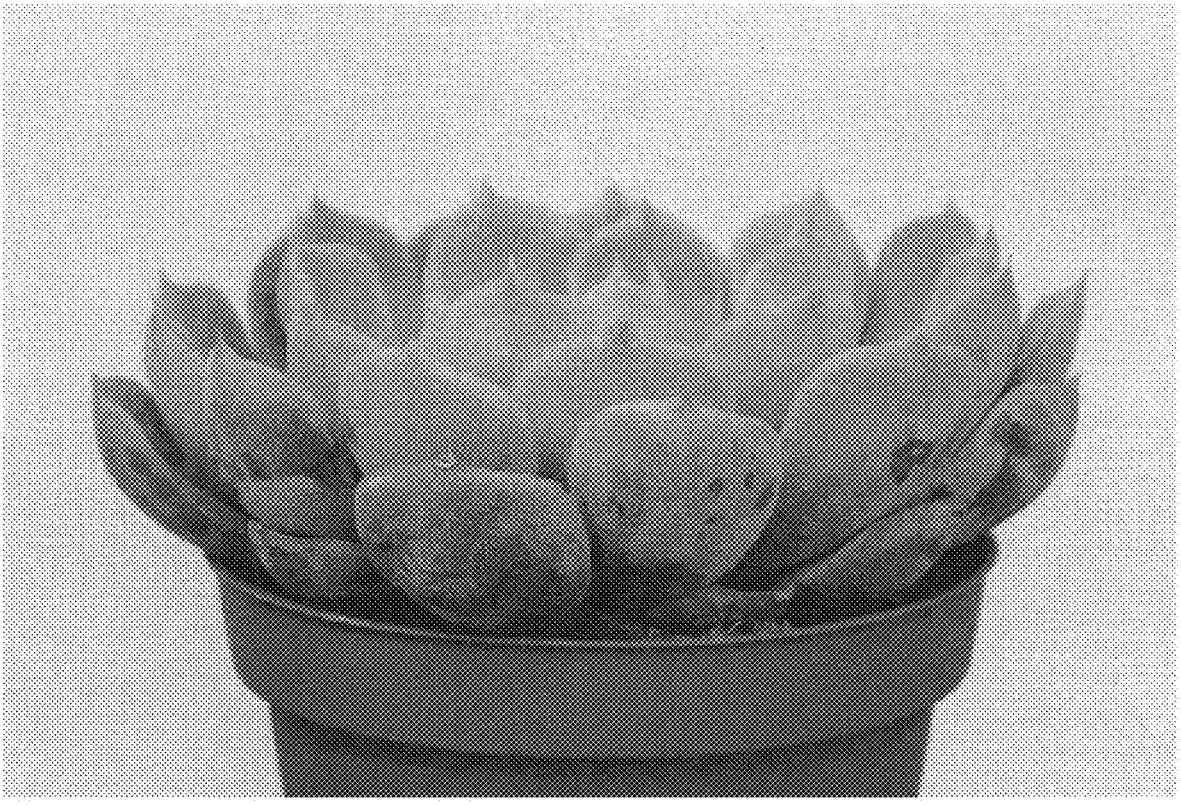
FIG. 1 illustrates, as nearly true as it is reasonably possible to make the same in color photographs of this type, an exemplary plant of 'TSAECH1824' grown in a commercial greenhouse in Heerhugowaard, the Netherlands. This plant is approximately 12 months old, shown planted in an 11 cm container.
Figure 2:
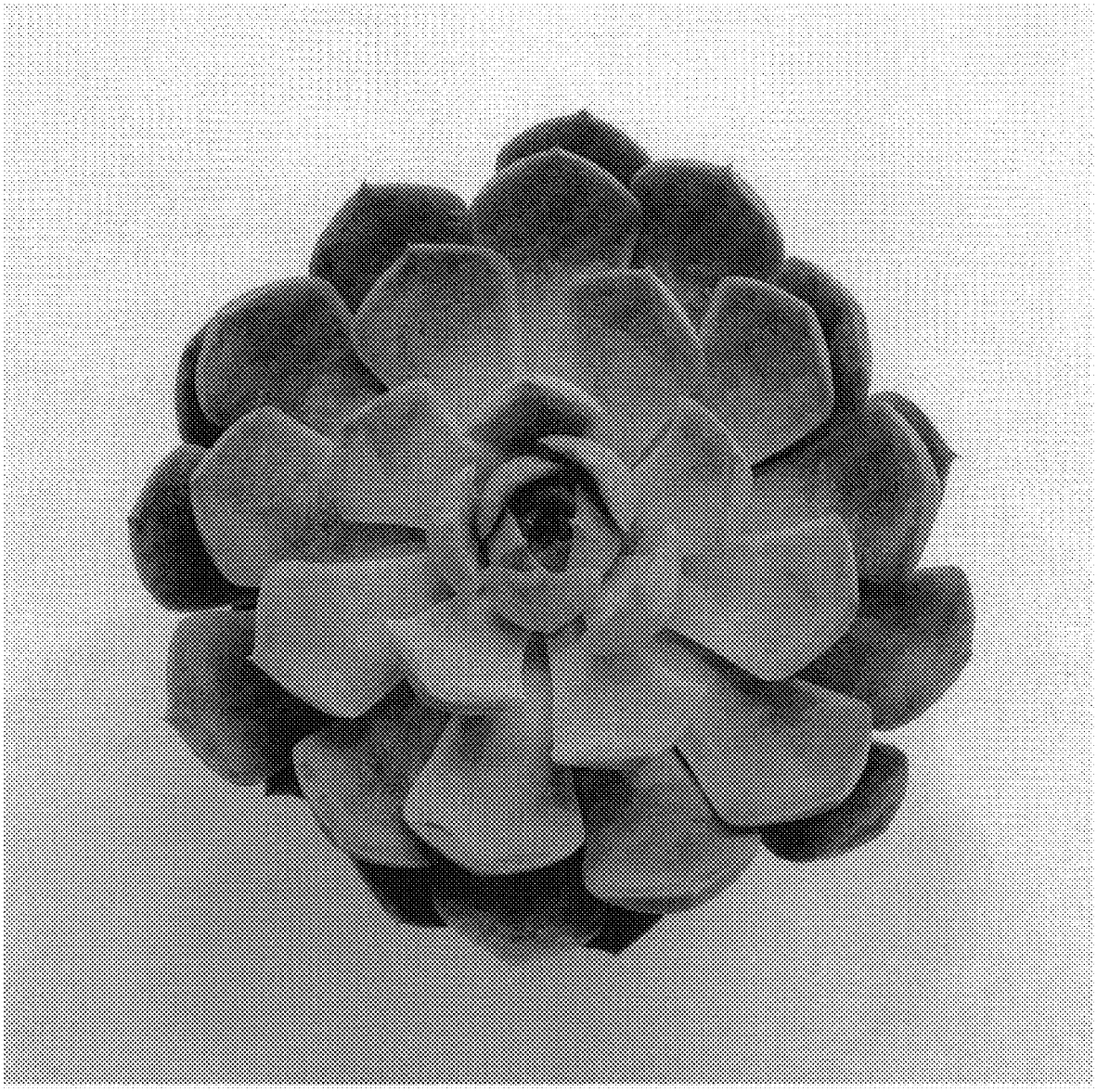
FIG. 2 illustrates, as nearly true as it is reasonably possible to make the same in color photographs of this type, the typical foliage arrangement of 'TSAECH1824'.
Figure 3:
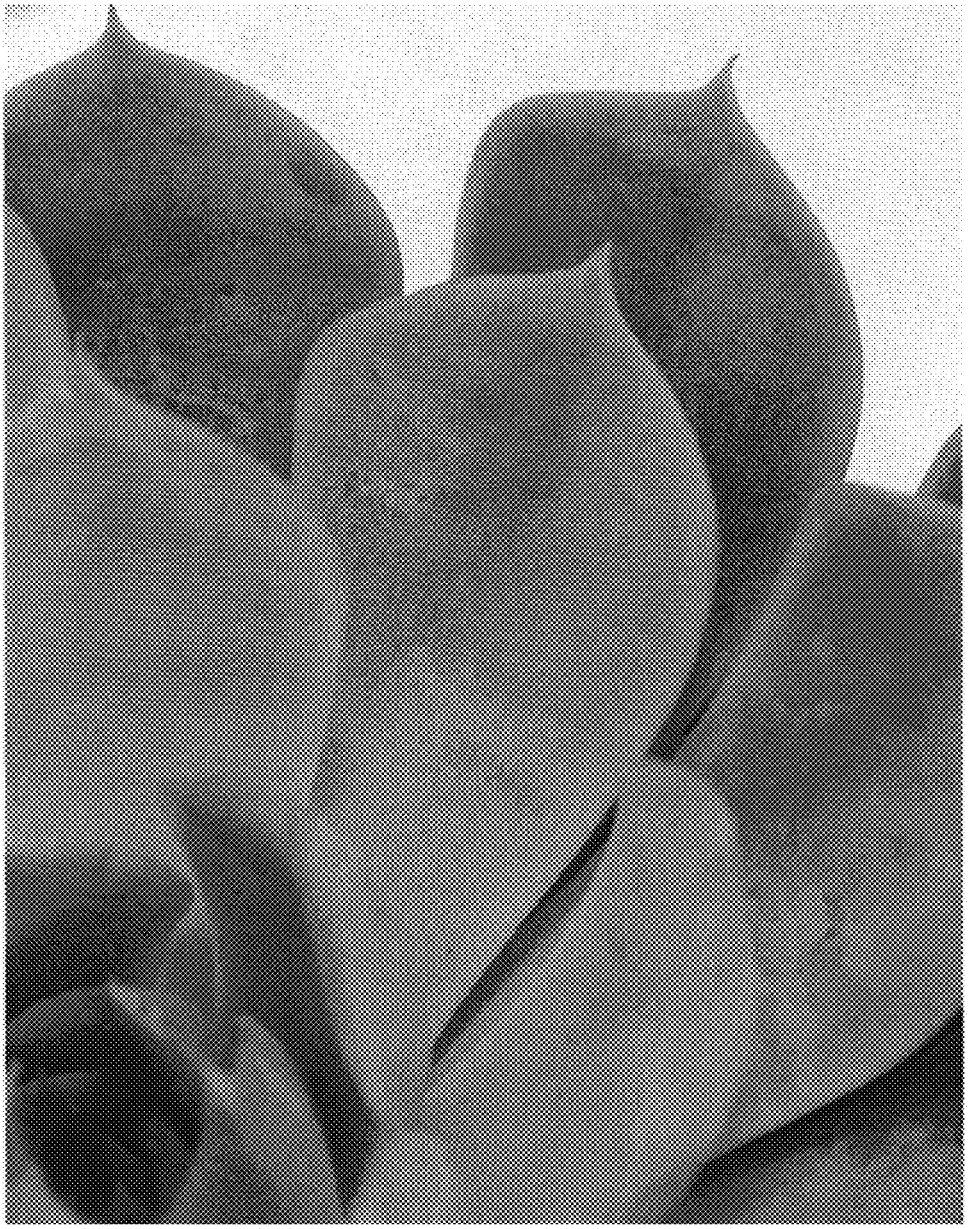
FIG. 3 illustrates, as nearly true as it is reasonably possible to make the same in color photographs of this type, the adaxial surface of the juvenile and mature foliage of 'TSAECH1824'.
Figure 4:
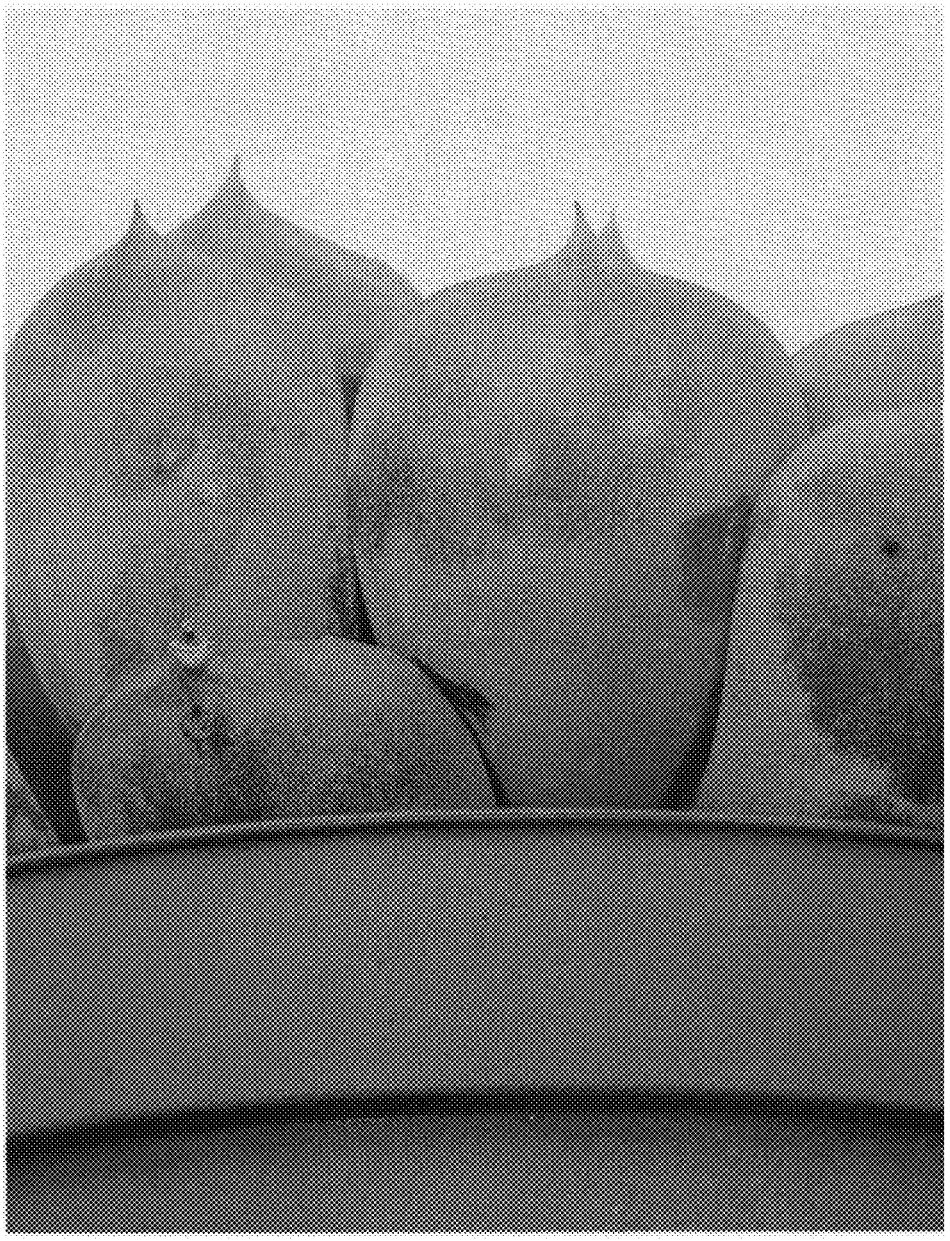
FIG. 4 illustrates, as nearly true as it is reasonably possible to make the same in color photographs of this type, the abaxial surface of the mature foliage of 'TSAECH1824'.

The following observations and measurements made in July of 2019 describe averages from a sample set of six specimens of 12 months old 'TSAECH1824' plants grown in 11 cm nursery containers at a commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1824' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1824' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—5.3 cm.

*Plant spread*.—Average of 12.9 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility*.—More resistant to insect pests known to infest *Echeveria* spp.; no more or less tolerant or resistant to pathogens known to infect *Echeveria* spp.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 40 leaves per rosette.

*Shape*.—Narrow obovate to broad oblanceolate.

*Dimensions*.—6.9 cm long, 2.7 cm wide, and 0.8 cm thick, on average.

*Aspect*.—Moderately concave and slightly curved upwards.

*Attitude*.—Both juvenile and mature foliage are held upright at an average angle of 30 degrees from vertical; outermost whorls are slightly more relaxed.

*Apex*.—Mucronate.

*Base*.—Long cuneate.

*Margin*.—Entire; not undulated.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Yellow-green, nearest to RHS N148A, and suffused with a darker yellow-green to greyed-green towards the apex, nearest to in between RHS N148A and 191A; fading to a lighter shade of yellow-green towards the base, nearest to RHS 147D; distally margined and tipped greyed-red, nearest to RHS 181B; the epicuticular wax covering the leaf surface is greyed-green, nearest to RHS 188A. Juvenile foliage, abaxial surface — Greyed-orange, nearest RHS 177C, and lightly suffused with greyed-green, nearest to RHS 197B; fading to yellow-green towards the base, nearest to RHS 147D; distally margined greyed-red, nearest to RHS 181C and tipped with a darker shade of greyed-red, nearest to RHS 181B; the epicuticular wax covering the leaf surface is greyed-purple, nearest to RHS N187D. Mature foliage, adaxial surface — Nearest to in between yellow-green and green, RHS 147A and NN137D, and fading to a lighter shade of yellow-green towards the base, nearest to RHS 146D; margined greyed-red, nearest to 179B; the epicuticular wax covering the leaf surface is greyed-green, nearest to RHS 188A. Mature foliage, abaxial surface — Greyed-green, nearest to RHS 194A, and suffused with greyed-red towards the apex, nearest to RHS 181C; margined greyed-red, nearest to RHS 179B; the epicuticular wax covering the leaf surface is greyed-purple, nearest to RHS N187D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1824' differ from the seed parent, an unnamed and unpatented *Echeveria lilacina* plant, in the following characteristics described in Table 1 below.

TABLE 1

| Characteristic | 'TSAECH1824' | Unnamed *Echeveria lilacina* seed parent. |
|---|---|---|
| General coloration of the foliage. | Generally appearing as a mixture of greyed-green and blue-green, suffused with lilac; margined and tipped pink. | Generally appearing as blue green. |

TABLE 1-continued

| Characteristic | 'TSAECH1824' | Unnamed *Echeveria lilacina* seed parent. |
|---|---|---|
| Foliage margin adoration. | More prominent than the seed parents | Less prominent than 'TSAECH1824'. |

Plants of the new cultivar 'TSAECH1824' differ from the pollen parent, *Echeveria* hybrid 'Perle von Nurnberg' (not patented), in the following characteristics described in Table 2 below.

TABLE 2

| Characteristic | 'TSAECH1824' | 'Perle von Nurnberg' |
|---|---|---|
| Plant profile. | Flattened. | Globular. |
| Foliage arrangement. | More loosely whorled. | More tightly whorled. |
| Foliage apex. | Mucronate, with a longer mucro than that of 'Perle von Nurnberg'. | Mucronate, with a shorter mucro than that of 'TSAECH1824'. |
| General coloration of the foliage. | Generally appearing as a mixture of greyed-green and blue-green, suffused with lilac; margined and tipped pink. | In between blue-grey and blue-green, generally presenting as a grey color due to heavy glaucosity. |

COMPARISONS WITH THE CLOSEST KNOWN COMPARATOR

Plants of the new cultivar 'TSAECH1824' differ from the closest known commercial comparator, the common form of the species *Echeveria* 'Orion' (U.S. Plant Pat. No. 26,228), in the following characteristics described in Table 3 below.

TABLE 3

| Characteristic | 'TSAECH1824' | 'Orion' |
|---|---|---|
| Foliage size. | Smaller than 'Orion'. | Larger than 'TSAECH1824'. |
| General coloration of the foliage. | Generally appearing as a mixture of greyed-green and blue-green; lilac suffusion is weaker than that of 'Orion'. | Generally appearing as a mixture of greyed-green and blue-green; lilac suffusion is stronger than that of 'TSAECH1824'. |
| Foliage margin coloration. | More prominent than 'Orion'. | Less prominent than 'TSAECH1824'. |

That which is claimed is:

1. A new and distinct variety of *Echeveria* plant named 'TSAECH1824', substantially as described and illustrated herein.

* * * * *